(12) United States Patent
Hunter

(10) Patent No.: US 10,274,470 B2
(45) Date of Patent: Apr. 30, 2019

(54) METHOD, APPARATUS, AND SYSTEM FOR DIAGNOSING AT LEAST ONE NOX-SENSOR OF A DIESEL ENGINE SYSTEM

(71) Applicant: DAF Trucks N.V., Eindhoven (NL)

(72) Inventor: Arjen Daniël Hunter, Eindhoven (NL)

(73) Assignee: DAF Trucks N.V., Eindhoven (NL)

(*) Notice: Subject to any disclaimer, the term of this patent is extended or adjusted under 35 U.S.C. 154(b) by 246 days.

(21) Appl. No.: 15/200,726

(22) Filed: Jul. 1, 2016

(65) Prior Publication Data
US 2017/0003259 A1    Jan. 5, 2017

(30) Foreign Application Priority Data

Jul. 3, 2015 (NL) ..................................... 2015086

(51) Int. Cl.
*G01N 21/00* (2006.01)
*G01N 27/00* (2006.01)
(Continued)

(52) U.S. Cl.
CPC ......... *G01N 33/0006* (2013.01); *F01N 11/00* (2013.01); *F02D 41/1461* (2013.01); *F02D 41/1463* (2013.01); *F02D 41/222* (2013.01); *G01M 15/102* (2013.01); *G01N 33/0037* (2013.01); *F01N 2560/026* (2013.01); *F01N 2560/14* (2013.01); *F01N 2900/0416* (2013.01); *F01N 2900/08* (2013.01);
(Continued)

(58) Field of Classification Search
CPC ............ G01N 33/0037; F02D 41/1461; F02D 41/1463

USPC .................. 73/1.06; 701/29.7, 29.9; 204/401
See application file for complete search history.

(56) References Cited

U.S. PATENT DOCUMENTS 5,771,686 A * 6/1998 Pischinger et al. .......................... B01D 53/9495 60/274
8,225,595 B2 * 7/2012 Garimella et al. .......................... B01D 53/9409 60/274

(Continued)

FOREIGN PATENT DOCUMENTS

EP    2128396 A1    12/2009
FR    2852395 A1    9/2004
(Continued)

*Primary Examiner* — Lisa M Caputo
*Assistant Examiner* — Roger G Hernandez-Prewitt
(74) *Attorney, Agent, or Firm* — Banner & Witcoff, Ltd.

(57) ABSTRACT

A method and apparatus for field testing an $NO_x$-sensor in a diesel engine exhaust system are disclosed. The apparatus is connectable to a truck having a lean burn diesel type engine, via an on-board diagnostic connector. A test cycle is performed on a running engine in at least two different states of operation, while $NO_x$ related values issued by the at least one $NO_x$-sensor are measured over a predefined period of time. One state of operation is obtained by simultaneously opening the exhaust gas recirculation valve and controlling the back pressure valve for increasing backpressure. A dedicated algorithm is used to compare the measured values to a predefined model, and to provide a numerical summary and statistical evaluation of the sensor functioning.

21 Claims, 4 Drawing Sheets

(51) Int. Cl.
*G01N 31/00* (2006.01)
*G01N 33/00* (2006.01)
*G01N 35/00* (2006.01)
*G01N 37/00* (2006.01)
*G01M 15/10* (2006.01)
*F01N 11/00* (2006.01)
*F02D 41/14* (2006.01)
*F02D 41/22* (2006.01)
*F02D 41/26* (2006.01)
*F02D 41/00* (2006.01)

(52) U.S. Cl.
CPC ...... *F02D 41/0037* (2013.01); *F02D 41/1441* (2013.01); *F02D 41/266* (2013.01); *Y02T 10/47* (2013.01)

(56) References Cited

U.S. PATENT DOCUMENTS

| | | |
|---|---|---|
| 2004/0010364 A1 | 1/2004 | Yasui et al. |
| 2009/0013666 A1 | 1/2009 | Jung |
| 2009/0229356 A1* | 9/2009 | Kariya et al. ......... F02D 41/146 73/114.73 |
| 2012/0255277 A1 | 10/2012 | Rajagopalan et al. |
| 2012/0303206 A1 | 11/2012 | Rajagopalan et al. |
| 2015/0113953 A1 | 4/2015 | Nilsson |

FOREIGN PATENT DOCUMENTS

| | | |
|---|---|---|
| WO | 2015002591 A1 | 1/2015 |
| WO | 2015048981 A1 | 4/2015 |

* cited by examiner

METHOD, APPARATUS, AND SYSTEM FOR DIAGNOSING AT LEAST ONE NOX-SENSOR OF A DIESEL ENGINE SYSTEM

CROSS-REFERENCE TO RELATED APPLICATIONS

This application claims the benefit of priority under 35 U.S.C. § 119 to Dutch patent application NL 2015086, filed Jul. 3, 2015, the contents of which are hereby incorporated by reference in their entirety.

FIELD OF THE INVENTION

The invention relates to a field service application for diagnosing $NO_x$-sensors in a vehicle exhaust system.

BACKGROUND OF THE INVENTION

Nitrogen oxides, generally referred to as "$NO_x$", are harmful for the environment. For some time $NO_x$-sensors are in common use with diesel engine vehicles as part of legal requirements regarding $NO_x$ emissions. The $NO_x$-sensors used in high power diesel applications in heavy freight trucks are derived from $NO_x$-sensors for the mainstream passenger car market. As a result the lifetime of the current $NO_x$-sensors is much shorter than the designed lifetime of high powered freight vehicle diesel engines. Typically the current $NO_x$-sensors have a lifespan of 200,000 to 300,000 road kilometers, whereas heavy trucks with diesel engines are designed to last between at least 1,200,000 to 1,600,000 road kilometers. This requires the $NO_x$-sensors in heavy trucks to be checked and replaced on a regular basis. To properly check the correct functioning of an $NO_x$-sensor it is currently necessary to remove these sensors from the vehicle's exhaust system and to have these tested by specialist testing services having the necessary costly apparatus to do so. Moreover the removal of these delicate $NO_x$-sensors from an exhaust system also requires sealing arrangements to be renewed upon reinstallation. The risk therefor exists that the sensor is rendered defective by the test itself. As a result of more recent legislation vehicles equipped with $NO_x$-sensors now also are required to have an on-board warning system to signal to the driver a possibly defective $NO_x$-sensor. Such warning systems initiate a workshop visit to enable any malfunctioning of $NO_x$-sensors to be excluded or to be corrected. Since adequate means for diagnosing $NO_x$-sensors is unavailable in most workshops, more often than not expensive $NO_x$-sensors are being replaced that turn out not to be defective, because the $NO_x$-sensor warning was caused by another defect. This phenomenon has caused unnecessary high costs for truck owners, and also led to unnecessary warranty costs for truck manufacturers.

SUMMARY OF THE INVENTION

Accordingly a need is felt to be able to test $NO_x$-sensors in vehicle exhausts without dismounting the $NO_x$-sensors, and with the vehicle in a stationary condition, while in a workshop. It would further be desirable for such a testing method and device not to require use of additional sample materials, such as $NO_x$ reference or test gases.

Accordingly it is an object of the present invention to propose an improved method and setup for in situ $NO_x$-sensor diagnosis. In a more general sense it is thus an object of the invention to overcome or reduce at least one of the disadvantages of the prior art. It is also an object of the present invention to provide alternative solutions which are less cumbersome in assembly and operation and which moreover can be made relatively inexpensively. Alternatively it is an object of the invention to at least provide a useful alternative.

To this end the invention provides for a method, an apparatus, and a system as defined in one or more of the appended claims.

The present diagnostic test uses operational conditions that can be achieved in a workshop with a stationary vehicle, and allows an accurate and reliable diagnosis in spite of $NO_x$ production levels that are necessarily limited to only 10% to 15% of those available when driving under heavy load. Thereby allowing for an accurate and reliable diagnosis by sensor response analysis in a range limited from the sensor minimum to 13-20% (400-600 ppm $NO_x$) of the measurable range (3000 ppm $NO_x$) of the sensor.

A method according to the invention for diagnosing at least one $NO_x$-sensor in a diesel engine system, may include providing a diesel engine, an inlet, an exhaust, and an exhaust gas after treatment system. The method may also include providing an exhaust gas recirculation system arranged to selectively connect the exhaust with the inlet. The method may further include providing a back pressure valve in the exhaust and an exhaust gas recirculation valve in the exhaust gas recirculation system for selectively connecting the exhaust to the inlet. The method may even further include providing at least one $NO_x$-sensor, wherein the at least one $NO_x$-sensor is located downstream of the back pressure valve in the exhaust. The method may include providing an electronic control unit arranged for reading the at least one $NO_x$-sensor, for controlling the exhaust gas recirculation valve and back pressure valve. The method may comprise testing steps, such as the step of running the engine in one state of operation, with one $NO_x$ production level. The method may further comprise the testing step of a first reading of the at least one $NO_x$-sensor values over a predefined time interval using the electronic control unit. The method may further also comprise the testing step of running the diesel engine in another state of operation. The state of operation being different from the one state of operation, with another $NO_x$ production level. The other $NO_x$ production level is lower than the one $NO_x$ production level. The other state of operation is obtained by opening the exhaust gas recirculation valve and controlling the back pressure valve for controlling the backpressure. The method may further comprise the testing step of a second values reading of the at least one $NO_x$-sensor over another predefined time interval using the electronic control unit. In such a method the at least one $NO_x$-sensor can be one of a first $NO_x$-sensor and a second $NO_x$-sensor, when the exhaust gas after treatment system may further comprise: a diesel fuel doser; a diesel oxidation catalyst; a diesel particulate filter; an exhaust reduction fluid doser; a selective catalyst reduction system; an ammonia oxidation catalyst; and wherein the second $NO_x$-sensor is located downstream of the ammonia oxidation catalyst in the exhaust. The method further may comprise the testing steps of: a first reading of the second $NO_x$-sensor values over a predefined time interval using the electronic control unit, wherein the engine is in the one state of operation; activating the exhaust reduction fluid doser, for dosing of exhaust reduction fluid into the exhaust; and a second reading of the second $NO_x$-sensor values over yet another predefined time interval using the electronic control unit. In this method the exhaust gas after treatment system may then further comprise: a pressure sensor, wherein the pressure sensor is a differential pressure sensor arranged for measuring the pressure difference over the diesel particulate filter. The method also comprises creating preliminary conditions before the testing steps, wherein the steps of creating the preliminary conditions comprise: running the diesel engine in a preliminary state of operation, in which the diesel runs idle at a first temperature; instructing the electronic control unit to close the exhaust gas recirculation valve; causing the exhaust gas recirculation valve to close; controlling the back pressure valve for increasing the temperature of the exhaust gas from the first temperature to a temperature, which is sufficiently high that soot can be burned off from the diesel particulate filter. The method further comprises measuring the pressure difference over the diesel particulate filter using the differential pressure sensor and using the electronic control unit for checking whether the exhaust reduction fluid doser is open; and for closing the exhaust reduction fluid doser when found open; checking whether the diesel fuel doser is open; opening the diesel fuel doser if found closed, for supplying diesel fuel to the diesel oxidation catalyst using the electronic control unit; regenerating the diesel particulate filter.

The method of the invention may also further comprises data analysis of the at least one $NO_x$-sensor, wherein the analysis comprises the steps of: using the first and second readings of the at least one $NO_x$-sensor to determine statistical values of the at least one $NO_x$-sensor; placing the statistical values in a matrix; comparing the statistical values to stored predefined statistical values from a predefined model; and determining the functioning of the at least one $NO_x$-sensor. As part of such a method the at least one $NO_x$-sensor can again be one of a first and a second $NO_x$-sensor, and the statistical values can comprise a value representative of a statistical minimum and a value representative of a statistical maximum of each of the first and second $NO_x$-sensors at a first and second reading thereof. Then optionally comparing the statistical values to a predefined model can comprise: using a statistical algorithm to establish a measure of linear correlation between the statistical values and the stored predefined statistical values, wherein the manner of linear correlation is expressed in a correlation coefficient; performing a linearity test; and determining linear deviation. As part of this option the statistical algorithm used to establish a measure of linear correlation between the statistical values and the stored predefined statistical values can be a Pearson algorithm, wherein the correlation coefficient is the product-moment correlation coefficient. As a further alternative the linearity test can also comprise: expressing a series of points in two-dimensional coordinates, where each point is formed by expressing a statistical value as a first dimensional part of the coordinates of the point and the predetermined statistical value as a second dimensional part of the coordinates of the point; and fitting a first order equation using a method of least squares to the series of points, wherein the coefficient of determination is used to determine the linearity of the series of points. In combination with such options determining the linear deviation may further comprise: expressing the linear deviation as the deviation of statistical values from the predetermined statistical values, wherein the linear deviation is expressed in percentile deviation from the predetermined statistical values.

Generally the diagnostic method according to the invention can be a computer implemented method. The software for such a computer implemented diagnostic method is conveniently stored on a non-transitory memory device.

The invention also relates to a diagnostic system that comprises a diesel engine system, with the diesel engine system including a diesel engine, having an inlet, an exhaust and an exhaust gas after treatment system, the exhaust and an exhaust gas recirculation system being arranged to connect the exhaust with the inlet, wherein the exhaust comprises a back pressure valve, and wherein the exhaust gas recirculation system comprises an exhaust gas recirculation valve; at least one $NO_x$-sensor located downstream of the back pressure valve in the exhaust; and an electronic control unit arranged for reading the at least one $NO_x$-sensor, for controlling the exhaust gas recirculation valve and for controlling the back pressure valve; wherein the diagnostic setup further comprises a diagnostic apparatus, wherein the diagnostic apparatus is arranged for being communicatively connectable to the electronic control unit of the diesel engine system, and wherein the diagnostic apparatus comprises a computer unit arranged for receiving, storing and processing data read from the at least one $NO_x$-sensor. In such a diagnostic system the at least one $NO_x$-sensor can be one of a first and a second $NO_x$-sensor, wherein the exhaust gas after treatment system further may comprise: a diesel fuel doser; a diesel oxidation catalyst; a diesel particulate filter; an exhaust reduction fluid doser; a selective catalyst reduction system; an ammonia oxidation catalyst; wherein the second $NO_x$-sensor is located downstream of the ammonia oxidation catalyst in the exhaust; and wherein the diagnostic apparatus is further arranged for receiving, storing and processing data read from the second $NO_x$-sensor.

In such a system the exhaust gas after treatment system may optionally further comprises: a pressure sensor, wherein the pressure sensor is a differential pressure sensor arranged for measuring the pressure difference over the diesel particulate filter; and wherein the diagnostic apparatus is arranged for determining the progress of regeneration of the diesel particulate filter using the measured pressure difference.

Optionally or alternatively in the diagnostic system of the invention the diagnostic apparatus can further be arranged for performing the analysis of the at least one $NO_x$-sensor, wherein the analysis comprises the steps of: using first and second readings of the at least one $NO_x$-sensor to determine statistical values of the least one $NO_x$-sensor; placing the statistical values in a matrix; comparing the statistical values to stored predefined statistical values from a predefined model; and determining the functioning of the at least one $NO_x$-sensor. In this optional or alternative system the diagnostic apparatus may form the statistical values using first and second readings of the at least one $NO_x$-sensor. In this regard the at least one $NO_x$-sensor may again be one of a first and a second $NO_x$-sensor, and the statistical values then can be a value representative of a statistical minimum and a value representative of a statistical maximum of each of the first and second $NO_x$-sensor at a first and second reading thereof.

The diagnostic system may optionally also have its diagnostic apparatus arranged for comparing the statistical values to a predefined model using at least one of a statistical algorithm for establishing correlation, a linearity test and a linear deviation. Then it can be advantageous when the statistical algorithm is a Pearson algorithm and the established correlation is linear.

In the diagnostic system optionally the diagnostic apparatus may further be arranged for sending instructions to the electronic control unit related to the controlling of the back pressure valve.

The diagnostic apparatus can further also be arranged for sending instructions to the diesel fuel doser and to the exhaust reduction fluid doser. Additionally the diagnostic apparatus may then be further arranged for relaying to an operator information pertaining the functioning of the at least one $NO_x$-sensor.

In a diagnostic apparatus according to the invention for diagnosing at least one $NO_x$-sensor in a diesel engine system, the diesel engine system can include a diesel engine, having an inlet, an exhaust, and an exhaust gas after treatment system, and further comprise: an exhaust gas recirculation system arranged to connect the exhaust with the inlet, wherein the exhaust comprises a back pressure valve, and wherein the gas recirculation system comprises an exhaust gas recirculation valve; wherein the at least one $NO_x$-sensor is located downstream of the back pressure valve in the exhaust; and an electronic control unit arranged for reading the at least one $NO_x$-sensor, for controlling the exhaust gas recirculation valve and back pressure valve; wherein the diagnostic apparatus is communicatively connectable to the electronic control unit for receiving readings from the at least one $NO_x$-sensor, and wherein the diagnostic apparatus is further arranged for performing a diagnostic analysis on the at least one $NO_x$-sensor. In such an apparatus the at least one $NO_x$-sensor can be one of a first and a second $NO_x$-sensor, wherein the exhaust gas after treatment system further comprises a diesel fuel doser; a diesel oxidation catalyst; a diesel particulate filter; an exhaust reduction fluid doser; a selective catalyst reduction system; an ammonia oxidation catalyst; wherein the second $NO_x$-sensor is located downstream of the ammonia oxidation catalyst in the exhaust; and wherein the diagnostic apparatus is arranged for receiving the second $NO_x$-sensor readings, and wherein the diagnostic apparatus is further arranged for performing the diagnostic analysis on the second $NO_x$-sensor.

The diagnostic apparatus, when the exhaust gas after treatment system further comprises: a pressure sensor, wherein the pressure sensor is a differential pressure sensor arranged for measuring the pressure difference over the diesel particulate filter; can also be arranged for receiving and interpreting readings from the pressure sensor to determine the progress of a regeneration of the diesel particulate filter.

In the diagnostic apparatus performing the analysis may also comprise: using first and second readings of the at least one $NO_x$-sensor to determine statistical values of the at least one $NO_x$-sensor; placing the statistical values in a matrix; comparing the statistical values to stored predefined statistical values from a predefined model; and determining the functioning of the at least one $NO_x$-sensor. Then as an alternative option the statistical values can be formed using first and second readings of the at least one $NO_x$-sensor. As an additional option the statistical values can comprise a value representative of a statistical minimum and a value representative of a statistical maximum of the at least one $NO_x$-sensor at a first and second reading thereof.

Also the diagnostic apparatus can be preprogrammed for comparing the statistical values to a predefined model: using a statistical algorithm to establish a measure of correlation between the statistical values of the at least one $NO_x$-sensor and the stored predefined statistical values, wherein the manner of linear correlation is expressed in a correlation coefficient; performing a linearity test; and determining linear deviation. Optionally the diagnostic apparatus may also be preprogrammed for using one of a linear, quadratic, polynomial, exponential and logarithmic correlation algorithm as the statistical algorithm. As a particular option the correlation algorithm can be a Pearson algorithm as the statistical algorithm, and the correlation coefficient can be the product-moment correlation coefficient. With this option the diagnostic apparatus can also be arranged for expressing the linear deviation as the deviation of statistical values from predetermined statistical values, wherein the linear deviation is expressed in percentile deviation from the predetermined statistical values.

The diagnostic apparatus of the invention can also be preprogrammed to perform the linearity test by: expressing a series of points in two-dimensional coordinates, where each point is formed by expressing a statistical value as a first dimensional part of the coordinates of the point and the predetermined statistical value as a second dimensional part of the coordinates of the point; and fitting a first order equation using a method of least squares to the series of points relating to the at least one $NO_x$-sensor, wherein the coefficient of determination is used to determine the linearity of the series of points belonging to the at least one $NO_x$-sensor.

The diagnostic apparatus can optionally also be arranged for determining the linear deviation by: expressing the linear deviation as the deviation of statistical values from the predetermined statistical values, wherein the linear deviation is expressed in percentile deviation from the predetermined statistical values.

Optionally the diagnostic apparatus can further be arranged for sending commands to the electronic control unit for adjusting the back pressure valve and the exhaust gas recirculation valve. In combination therewith the apparatus may further be arranged for sending commands to the electronic control unit for adjusting diesel fuel doser and the exhaust reduction fluid doser. Alternatively the at least one $NO_x$-sensor can be one of a first and a second $NO_x$-sensor, wherein the apparatus is further preprogrammed for performing a testing sequence, wherein the testing sequence comprises: running the engine in one state of operation, with one $NO_x$ production level; a first reading of the first $NO_x$-sensor values over a predefined time interval using the electronic control unit; running the engine in another state of operation, with another $NO_x$ production level, wherein the third $NO_x$ production level is lower than the second $NO_x$ production level, wherein the other state of operation is obtained by opening the exhaust gas recirculation valve and controlling the back pressure valve for controlling the back-pressure; and a second reading of the first $NO_x$-sensor values over another predefined time interval using the electronic control unit. In this regard the testing sequence may further comprise: a first reading of the second $NO_x$-sensor values over a predefined time interval using the electronic control unit, wherein the engine is in the one state of operation; opening the exhaust reduction fluid doser, for the dosing of exhaust reduction fluid into the exhaust; and a second reading of the second $NO_x$-sensor values over yet another predefined time interval using the electronic control unit.

It is also possible for the apparatus to be preprogrammed for creating preliminary conditions before the testing steps, wherein the steps of creating the preliminary conditions can comprise: running the diesel engine in a preliminary state of operation, wherein the diesel runs idle at a first temperature; instructing the electronic control unit to close the exhaust gas recirculation valve; closing the exhaust gas recirculation valve; controlling the back pressure valve for increasing the temperature of the exhaust gas from the first temperature to a temperature which is sufficiently high that the soot can be burned off further upstream in the exhaust; checking if the diesel fuel doser is open; opening the diesel fuel doser if found closed, for supplying diesel fuel to the diesel oxidation catalyst using the electronic control unit; regenerating the diesel particulate filter; measuring the pressure difference over the diesel particulate filter using the pressure sensor and using the electronic control unit; checking whether the exhaust reduction fluid doser is open; and closing the exhaust reduction fluid doser when found open.

The diagnostic apparatus may optionally also comprise: a programmable computer unit, programmed for performing the analysis; a communication unit, for communicating to one of the electronic control unit, a separate computer, a tablet, a smartphone, a television screen and a computer screen; a data storage unit, for storing data related to the analysis; a human interface; and a display. In such an apparatus the programmable computer unit may comprise a processing unit, programmed for performing the analysis. In this regard the communications unit can be one of connectable to an on board diagnostics port and connectable directly to the electronic control unit. As an alternative option the communications unit may also be one of a wireless communication arrangement, such as Bluetooth, and a communications port for cables. The data storage unit can be a non-volatile memory such as a flash memory, a memory card, a USB flash drive, a solid state drive or a hard disk drive. The human interface and display, when present, can be one single unit, such as a touch screen, or include separate units, when the interface comprises a separate keyboard. The apparatus can also comprise an on board power supply. When the apparatus is also arranged for sending commands to the electronic control unit for adjusting diesel fuel doser and the exhaust reduction fluid doser, it may also further be arranged for sending commands to the electronic control unit for managing at least one of a rate of fuel consumed by the diesel engine and an engine rotation frequency.

Generally the diagnostic apparatus according to the invention can be a computer programmed diagnostic apparatus. The software for such a computer programmed diagnostic apparatus is conveniently stored on a non-transitory memory device.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

DETAILED DESCRIPTION OF THE INVENTION

Figure 1:
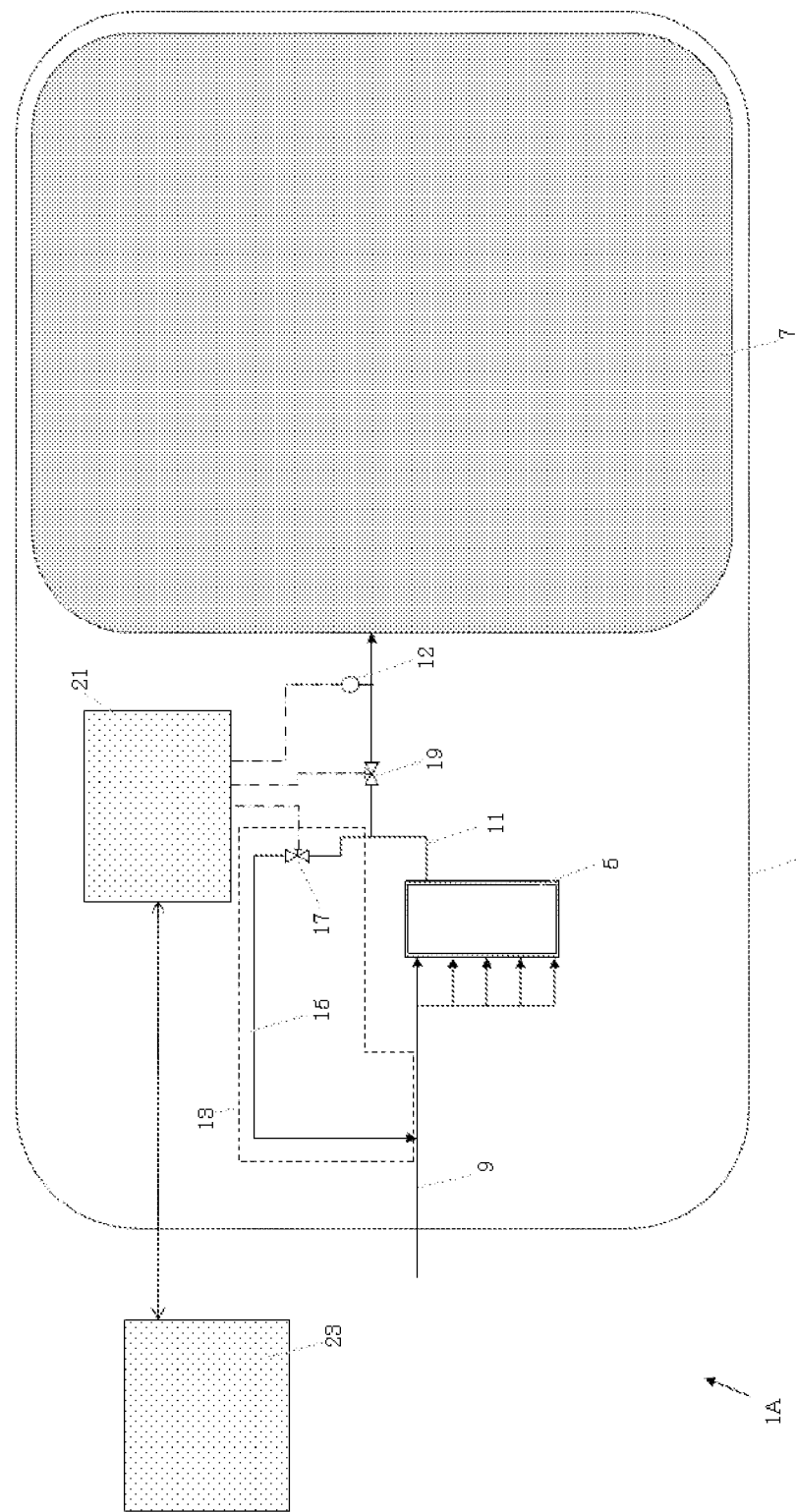
FIG. 1 shows a diagnostic setup for diagnosing a first $NO_x$-sensor in a diesel engine system.

In FIG. 1 a diagnostic setup 1A for diagnosing $NO_x$-sensor performance in a diesel engine system 3 is schematically illustrated. In the diagnostic setup of FIG. 1 the diesel engine system 3 includes a diesel engine 5 and an exhaust after treatment system (EAS) 7 for after treatment of exhaust gas. The diesel engine system 3 further comprises a first $NO_x$-sensor 12 associated with an upstream end of a diesel engine exhaust after treatment system 7. The diesel engine 5 further comprises an inlet 9, an exhaust 11 and an exhaust gas recirculation system or EGR system 13. The EGR system 13 is defined as an exhaust gas path 15 with an exhaust gas recirculation valve or EGR valve 17. The EGR system 13 connects the exhaust 11 to the inlet 9. The exhaust 11 in turn has a back pressure valve or BPV 19, for regulating the back pressure. The first $NO_x$-sensor 12 is positioned downstream of the BPV 19 in the exhaust 11 for allowing $NO_x$-levels to be measured in exhaust gas passing through the exhaust 11. To achieve the second state of operation of the diesel engine 5 the BPV 19 is required to be in an open position and the EGR valve 17 is required to be closed. To achieve the third state of operation the BPV 19 and the EGR valve 17 must be controlled so as to achieve sufficient recirculation of exhaust gas to the diesel engine 5.

The diesel engine system 3 is further provided with an electronic control unit or ECU, which is arranged as engine control unit ECU 21. The ECU 21 is arranged for receiving data and instructions related to controlling the EGR valve 17 and the BPV 19. The ECU 21 is preprogrammed to control the exhaust after treatment system 7, amongst others by means of the EGR valve 17 and the BPV 19, so that a predefined engine performance can be achieved.

The EGR valve 17 and the BPV 19 are each controllable to achieve normal operations. The normal operations of the EGR valve 17 and the BPV 19 are predefined by the ECU 21. Normal operations means that the settings of the EGR valve 17 and the BPV 19 are controlled by the ECU 21 to achieve one of a high fuel economy and a low $NO_x$ production and a predefined point between high fuel economy and low $NO_x$ production for the diesel engine 5 during normal operational conditions thereof. The ECU 21 is also arranged for reading the value of the first $NO_x$-sensor 12 related to the $NO_x$ level in the exhaust at the location of the first $NO_x$-sensor 12.

The diesel engine 5 is able to operate in a plurality of predetermined states of operation, wherein the states of operation include at least one of a first state of operation, a second state of operation and a third state of operation. In the first state of operation the diesel engine 5 runs idle and without load. In the first state of operation the diesel engine 5 further operates at a first exhaust gas temperature and a first $NO_x$ production level associated with the diesel engine 5 running idle and without a load. In the second state of operation the diesel engine 5 operates substantially at a second exhaust gas temperature and has a second $NO_x$ production level associated therewith. In the second state of operation, the second exhaust gas temperature is higher than the first exhaust gas temperature and the second $NO_x$ production level is higher than the first $NO_x$ production level. In the third state of operation the diesel engine 5 operates a third exhaust gas temperature and a third $NO_x$ production level associated therewith. Here, the third exhaust gas temperature is lower than the second exhaust gas temperature and the third $NO_x$ production level is lower than the second $NO_x$ production level.

The diagnostic setup 1A further comprises a diagnostic apparatus 23, which is communicatively connectable to the ECU 21. The diagnostic apparatus 23 is communicatively connectable to the ECU 21 via a standardized hardware interface such as a connection port designed for on-board diagnostics specifically an OBD-II connector. Alternatively the diagnostic apparatus 23 can also be connectable via an Assembly Line Diagnostics Link or ALDL, an OBD-I connector, an EOBD connector, or a JOBD connector. In other embodiments the diagnostic apparatus 23 directly connects to the ECU 21. The diagnostic apparatus 23 is arranged for receiving readings related to the first $NO_x$-sensor 12 from the ECU 21. Additionally the diagnostic apparatus 23 is arranged for sending instructions or commands, to the ECU 21, which relate to controlling the BPV 19 and the EGR valve 17 for achieving at least the second and third state of operations described above.

Figure 2:
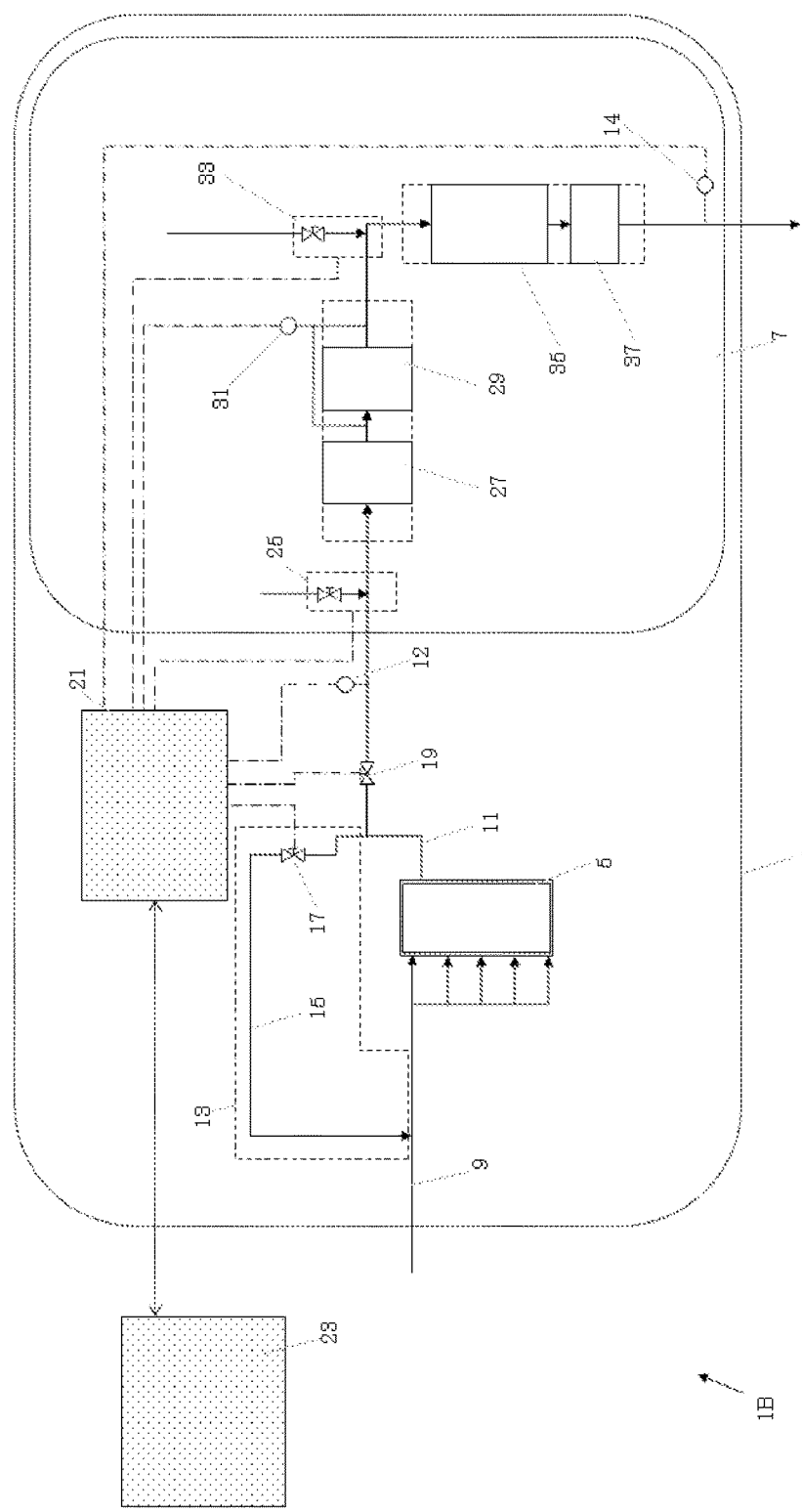
FIG. 2 shows a diagnostic setup for diagnosing first and second $NO_x$-sensors in a diesel engine system.

FIG. 2 shows another embodiment of the diagnostic setup 1B wherein the exhaust gas after treatment system (EAS) 7 of the diesel engine system 3 includes a diesel fuel doser 25 for dosing diesel fuel into the exhaust 11. The exhaust gas after treatment system 7 further comprises a diesel oxidation catalyst or DOC 27, a diesel particulate filter or DPF 29 and a differential pressure sensor 31 over the DPF 29 for monitoring the pressure drop over the DPF 29. The exhaust gas after treatment system 7 is further provided with an exhaust reduction fluid doser 33 for dosing exhaust reduction fluid into the exhaust 11. The reduction fluid in this example is an aqueous solution of high-purity urea in deionized water such as solutions compliant with the ISO 22241 standard. The solution is made with approximately 32.5% high-purity urea and approximately 67.5% deionized water. The exhaust gas after treatment system 7 further has a selective catalyst reduction or SCR system 35 and an ammonia oxidation catalyst 37. The exhaust gas after treatment system 7 in the example of FIG. 2 is equipped with a second $NO_x$-sensor 14 equipped for sensing $NO_x$ levels and thereby measuring $NO_x$ levels in the exhaust gas passing through the exhaust 11. The second $NO_x$-sensor 14 is positioned downstream of the ammonia oxidation catalyst 37. In the diesel engine system 3, as seen in FIG. 2, the ECU 21 is arranged to control the diesel fuel doser 25 and exhaust reduction fluid doser 33 and is further arranged to read the differential pressure sensor 31 and the second $NO_x$-sensor 14.

Figure 3:
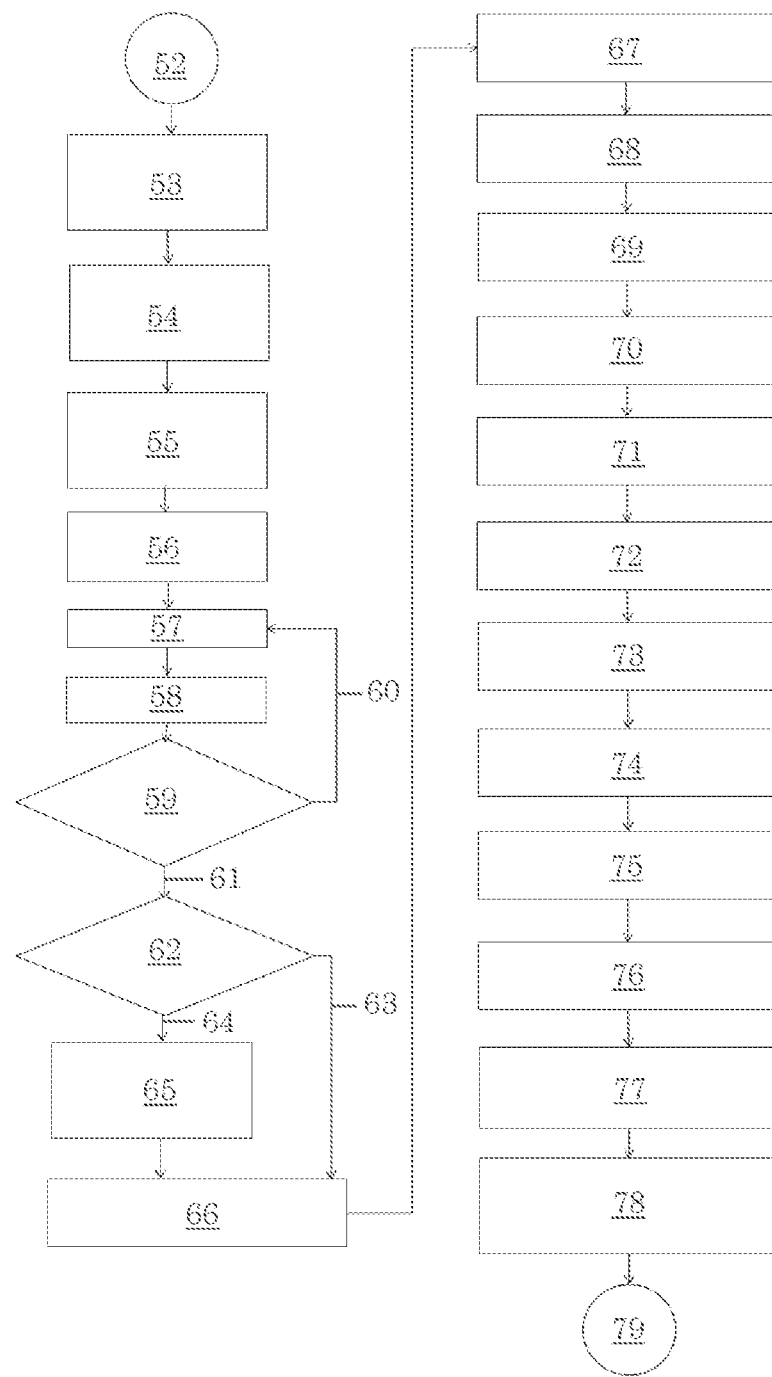
FIG. 3 schematically shows the method steps of the diagnostic method for diagnosing the first and a second $NO_x$-sensor in a diesel engine system.

In FIG. 3 a flowchart is shown of a method for in situ diagnostics of the first and second $NO_x$-sensor functionality in a diesel engine system according to FIG. 2. The method comprises creating preliminary conditions in the diesel engine system for initiating the testing sequence wherein data pertaining to the first and second $NO_x$-sensors 12, 14 are gathered, the testing sequence and performing the analysis of the data gathered in the testing sequence to determine the functionality of the $NO_x$-sensors.

Creating the preliminary conditions may comprise regenerating the DPF 29 and further ensuring that no exhaust reduction fluid is present in the exhaust. To accomplish the regeneration of the DPF 29 the diesel engine 5 is run in the above explained first state of operation. The ECU 21 is further instructed to close the EGR valve 17 and to control the BPV 19 such that that the exhaust gas heats the DPF 29 to a temperature at which regeneration occurs. The regeneration is performed at a temperature between 450-600° C. and above depending on the diesel engine system and may not exceed a temperature at which using or sustaining such a temperature for regeneration would entail thermal damage under the dosing of diesel fuel into the exhaust 11 by the diesel fuel doser 25. The temperature remains below a temperature at which damage occurs to elements associated with the exhaust 11. Regeneration is confirmed using the differential pressure sensor 31 over the diesel particulate filer (DPF) 29. To ensure that no exhaust reduction fluid is present in the exhaust the reduction fluid doser 33 is closed.

Performing the testing sequence starts with bringing the diesel engine 5 into the above explained second state of operation followed by a first reading of values of the first $NO_x$-sensor 12 and a first reading of values of the second $NO_x$-sensor 14 over a predefined time interval. This is done using the ECU 21. Which is followed by opening the exhaust reduction fluid doser 33 for dosing reduction fluid into the exhaust gas path 11, where after a second reading is performed of values of the second $NO_x$-sensor 14 over another predefined time interval. This is done using the ECU 21. After the second reading is completed the engine 5 is brought into the above explained third state of operation. In the third state of operation the diesel engine 5 further has a third exhaust gas temperature and a third $NO_x$ production level. The third exhaust gas temperature is lower than the second exhaust gas temperature and the third $NO_x$-production level is lower than the second $NO_x$-production level. The third state is obtained by opening the EGR valve 17, using the ECU 21, for allowing for recirculation of part of the exhaust gas and controlling the BPV 19 to further increase or decrease the recirculation by increasing or decreasing backpressure; this can also be referred to as restoring the diesel engine system to its normal operation. After achieving the third state, performing the testing sequence further comprises a second reading of values of the first $NO_x$-sensor 12 over yet another predefined time interval using the ECU 21.

The analysis performed using the first and second readings of the first and second $NO_x$-sensors serves to determine statistical values of the first and second $NO_x$-sensors. These statistical values are values representative of statistical minimum and values representative of statistical maximum values at each of the first and second $NO_x$-sensors at the first and second reading thereof. During each first and second reading of each first and second $NO_x$-sensors a measurement population of approximately 50-100 thousand data points is generated. It will be understood that the statistical minimum or maximum values can be one of a number of statistical values representative of the measurement population, such as representative of measured minimum and maximum values or a descriptive statistics minimum and maximum values associated with a normal distribution such as predetermined lower and upper quartiles in the distribution of a measurement population. Further, it will be understood that the statistical minimum and maximum values are pretreated to avoid the incorporation of outliers in the statistical values. Additionally it will be understood that statistical minimum or maximum values can be interpreted to be a single minimum or maximum value representative of the statistical mean value at each of the first and second $NO_x$-sensors at the first and second reading thereof, such as when measurements around a lower measurable limit yield non-normal data. The $NO_x$ levels as sensed by each of the first and second $NO_x$-sensors are read during a first and the second reading. During either the first or second reading the general $NO_x$-level at each of the first and second $NO_x$-sensors is the higher. The statistical minimum and maximum values associated with the higher $NO_x$-level are defined as a high $NO_x$-values. The statistical minimum and maximum values associated with the lower $NO_x$-level of the first and second readings are defined as the low $NO_x$ values.

The statistical values of each first and second $NO_x$-sensor thus are four statistical values, namely a statistical maximum value at high $NO_x$ levels, a statistical minimum value at high $NO_x$ levels, a statistical maximum value at low $NO_x$ levels, and a statistical minimum value at low $NO_x$ levels. The statistical values are placed in a matrix, where after the values are compared to the predefined statistical values from a predefined model. The predefined model is used as a benchmark data set derived from the statistical values of correctly functioning first and second $NO_x$-sensors 12,14 in a similar diesel engine system 3.

The analysis further comprises using a statistical algorithm to establish a measure of a correlation between the statistical values and the predefined statistical values. In this embodiment the established correlation is linear. Alternatively other correlations such as be quadratic, polynomial, exponential and logarithmic correlations are established if applicable. The level of correlation is expressed in a correlation coefficient. It will be understood that air density, humidity and mileage which are of effect on $NO_x$ production are confounding variables to the measured $NO_x$-level. It will be understood that the measurement of a $NO_x$-level contains information about confounding variables. It will further be understood that the predetermined statistical values can be interpreted to also being adjustable in accordance with the expected influence of confounding variables to match measurement conditions. A suitable statistical algorithm to determine the linear correlation is the Pearson algorithm. According to this algorithm the correlation coefficient in this algorithm is expressed as the product-moment correlation coefficient. In Table 1 the statistical values and corresponding predetermined statistical values are shown for a single $NO_x$-sensor, wherein the single $NO_x$-sensor represents one of the first and second $NO_x$-sensors 12, 14.

TABLE 1

| Statistical values | $NO_x$-sensor | Model |
|---|---|---|
| Statistical minimum at low $NO_x$ | $V_1$ | $M_1$ |
| Statistical maximum at low $NO_x$ | $V_2$ | $M_2$ |
| Statistical minimum at high $NO_x$ | $V_3$ | $M_3$ |
| Statistical maximum at high $NO_x$ | $V_4$ | $M_4$ |

In Table 1, $V_1$-$V_4$ represent the statistical values of the single $NO_x$-sensor and $M_1$-$M_4$ represent the corresponding predetermined statistical values from the predefined model. The values $V_1$-$V_4$, and $M_1$-$M_4$ are used to compute the product-moment correlation coefficient using the Pearson algorithm following Equation 1.

$$ppmcc = \frac{\sum_{i=1}^{n} V_i \cdot M_i - \frac{\left(\sum_{i=1}^{n} V_i\right) \cdot \left(\sum_{i=1}^{n} M_i\right)}{n}}{\sqrt{\left(\sum_{i=1}^{n} V_i^2 - \frac{\left(\sum_{i=1}^{n} V_i\right)^2}{n}\right) \cdot \left(\sum_{i=1}^{n} M_i^2 - \frac{\left(\sum_{i=1}^{n} M_i\right)^2}{n}\right)}}$$ Equation 1

$0 \leq |ppcmm| \leq 1$ $-1 \leq ppcmm \leq 1$

In Equation 1:
the ppmcc is the Product-moment correlation coefficient;
the $V_i$ is a statistical value as presented in Table 1;
the $M_i$ is a predetermined statistical value as presented in Table 1; and
the n is the number of the population, which equals the amount of statistical values which is compared. Here this number is 4.

Equation 2 shows how the sum components of the Pearson algorithm evolve when applying the algorithm to the statistical values presented in Table 1.

$$\sum_{i=1}^{4} V_i \cdot M_i = M_1 V_1 + M_2 V_2 + M_3 V_3 + M_4 V_4$$ Equation 2

$$\sum_{i=1}^{4} V_i = V_1 + V_2 + V_3 + V_4$$

$$\sum_{i=1}^{4} M_i = M_1 + M_2 + M_3 + M_4$$

$$\sum_{i=1}^{4} V_i^2 = V_1^2 + V_2^2 + V_3^2 + V_4^2$$

$$\sum_{i=1}^{4} M_i^2 = M_1^2 + M_2^2 + M_3^2 + M_4^2$$

It will be understood that the Pearson algorithm as seen in Equation 1 can be applied such that the product-moment correlation coefficient is representative of the Spearman's rank correlation coefficient. This can be obtained from Equation 1 by replacing each $V_i$ by its rank. The rank is the position of the size of the value of $V_i$ in ascending order. It will further be understood that the Pearson algorithm as seen in Equation 1 is further adapted making the product-moment correlation coefficient representative of a weighted correlation coefficient. It will further also be understood that the statistical values and predetermined statistical values can be normalized values. Equation 1 shows that the value of the absolute of the correlation coefficient can vary between 0-1, where approaching 0 means there to be no linear correlation present, and approaching 1 means there to be a full linear correlation. Additionally, the correlation coefficient can vary between −1 and 1, a negative value is here representative of an inverted linear correlation. The absence of a linear correlation, or finding of a reduced linear correlation or an inverted linear correlation is used as an indication that the representative first or second $NO_x$-sensors 12, 14 to which the statistical values relate is malfunctioning. Using the Pearson algorithm as specifically presented in Equation 1 a first indication of malfunctioning is determined when a correlation coefficient arises of 0.91 and lower, and preferably of 0.7 and lower, and even more preferably of 0.2 and lower with a lower limit of −1. A correlation coefficient of between 0.9 and 0.95 can be an indication of a non-linear deviation. It will be appreciated that similar boundary conditions may be implemented depending on the chosen application of the algorithm, such as having the algorithm be applied as normalized. Non-linear deviation is only considered an indication of a malfunctioning first or second $NO_x$-sensor 12, 14 in combination with other indications.

Further a linearity test is performed. In the linearity test a series of two-dimensional coordinates on a two-dimensional plane is expressed as points. Here each point is formed by expressing a statistical value, such as $M_1$, as a first dimensional part of the coordinates of the point and the corresponding predetermined statistical value, in the case of $M_1$ this is $V_1$, as a second dimensional part of the coordinates of the point. For each statistical value a point is formed. The series of points is then fitted with a first order equation using a method of least squares. The first order equation such as shown in Equation 3.

$$y = c_0 + c_1 x$$ Equation 3

In Equation 3:
the x represents the first dimension, associated with the predetermined statistical values $M_i$;

the y represents the second dimension, associated with the statistical values $V_i$;
the $c_0$ represents a zero order constant; and
the $c_1$ represents a first order constant;
the constants $c_0$ and $c_1$ represent a linear deviation. In a situation where the respective first or second $NO_x$-sensor 12, 14 responds the same as the model the equation will yield for $c_0$ a zero value, and for $c_1$ a value equal to unity. Unity is to be interpreted as the value 1. The fitted first order equation also possesses a coefficient of determination. The coefficient of determination describes how well the equation fits the points. The coefficient of determination is referred to as $R^2$ and is determined as presented in Equation 4.

$$R^2 = 1 - \frac{sum_{res}}{sum_{tot}}$$ Equation 4

$$sum_{res} = \sum_{i=1}^{n} (V_i - y_{(M_i)})^2$$

$$sum_{tot} = \sum_{i=1}^{n} \left(V_i - \frac{1}{n}\sum_{i=1}^{n}(V_i)^2\right)^2$$

In Equation 4 $R^2$ is the coefficient of determination, which is a value expressed as a function of a residual sum of squares, expressed as $sum_{res}$, and a total sum of squares, expressed as $sum_{tot}$.

The coefficient of determination expresses the overall linearity of the series of points in the two-dimensional plane. A coefficient of determination approaching 0 having a negative value is indicative of non-linearity and a coefficient of determination approaching 1 is indicative of the data being fully linear. Non-linearity is here also used as an indication that any of the first and second $NO_x$-sensors 12, 14 to which the statistical values relate is malfunctioning. The coefficient of determination can vary from any negative number to 1. A second indication of malfunctioning is when the coefficient of determination is below 0.9, and preferably below 0.83 and even more preferably below 0.7. Following the linearity test linear deviation is determined using the fitted first order equation as shown in Equation 3. The value of $c_1$ is inversely proportional to the linear deviation. Wherein the relation of the value of the linear deviation follows Equation 5.

$$dev \% = (c_1-1) \cdot 100\%$$ Equation 5

In Equation 5:
the dev % represents the linear deviation in percentage;
the $c_1$ represents the first order constant from the fitted first order equation;
a linear deviation of −20% and greater negative number is a third indication of a malfunctioning first or second $NO_x$-sensor 12, 14. Also positive linear deviation of +20% and above is considered a third indication of malfunctioning, more preferably any linear deviation, positive or negative, exceeds ±50%, and even more preferably linear deviation exceeds ±80% for being a third indication of malfunction. The corresponding values for $c_1$ follow from Equation 5. Additionally the fitted $c_0$ constant using Equation 3 demonstrates the linear offset thereof. The linear offset using non-normalized data exceeding the value of ±50, more preferably ±100 and even more preferably ±200 is a further indication of malfunction.

Alternatively the linear deviation is expressed as the deviation of the statistical values from the predetermined statistical values. The predetermined statistical values are expressed in a percentage of the value of the predetermined statistical values. If the linear deviation is −80% the statistical values are on average a factor 5 smaller than the predetermined values. A linear deviation between −80% and −100% is a third indication of malfunctioning, this is the same for a linear deviation of 80% and higher.

If the statistical values associated with the first and second $NO_x$-sensors 12, 14 in the analysis are found to be associated with both the first and second indications of malfunctioning the representative $NO_x$-sensor can be determined to be malfunctioning based on those first and second indications of malfunctioning.

The diagnostic apparatus 23 as presented in the examples of FIGS. 1 and 2 is arranged for performing the analysis as described. The diagnostic apparatus 23 interprets the measure of linear correlation, the linearity test and the linear deviation. The diagnostic apparatus 23 interprets data of the first and second $NO_x$-sensor 12, 14 according to the analysis. The diagnostic apparatus 23 is programmed to detect the first indication of malfunctioning at a correlation coefficient below a predetermined value therefor. The diagnostic apparatus is arranged for receiving the measured data for the first and second $NO_x$-sensors during the first and second measuring and for manual or via sensor receiving the humidity, air pressure or air density (altitude), the power of the engine power output or engine power output capacity and engine system. The diagnostic apparatus 23 is further arranged for determining and removing outliers from the measured data and taking a sample population for analysis. The diagnostic apparatus is further arranged for using the data in that sample for determining the statistical values.

The diagnostic apparatus 23 is further arranged for working independently from or in association with engine diagnostic programs such as the Paccar DAVIE program for performing the mentioned analysis for, and the reporting on, the first, second, third and other indications of a malfunctioning first or second $NO_x$-sensors.

Figure 4:
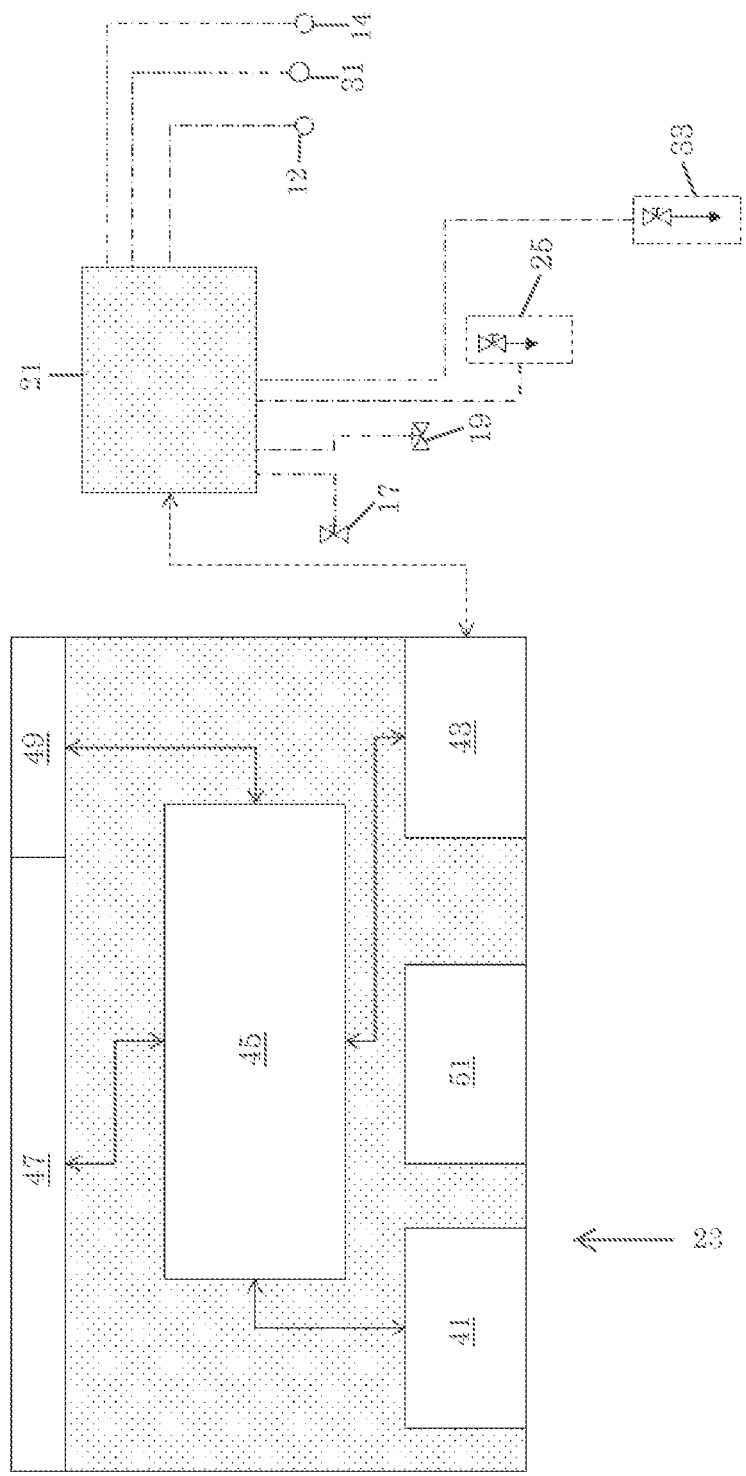
FIG. 4 shows an embodiment of a diagnostic apparatus.

The diagnostic apparatus 23 comprises, as schematically shown in FIG. 4, a display 47 and human interface 49 for displaying indications of a malfunctioning first and/or second $NO_x$-sensor 12, 14. The interface 49 is arranged to allow an operator to read the indications of malfunctioning from the display 47. The diagnostic apparatus 23 is further arranged to allow the operator to use the interface to display the matrix comprising the statistical values on the display 47. It is further also possible for the diagnostic apparatus 23 to be programmed to display a summary of the analysis on the display 47. The summary of the analysis can comprise the statistical values, the predetermined statistical values, the correlation coefficient, the fitted first order equation related to the linearity test, the coefficient of determination, and the percentage of linear deviation. Based on the summary and the indications of malfunctioning the operator is provided with sufficient information to determine whether the relevant $NO_x$-sensor is malfunctioning. In an alternative embodiment the diagnostic apparatus 23 is arranged to plot the first order equation and the points.

Alternatively, based on the interpretation of the measure of linear correlation, the linearity test and the linear deviation relating to any one of the first and second $NO_x$-sensor 12, 14 the diagnostic apparatus 23 is arranged for rejecting the related first or second $NO_x$-sensor 12, 14 without requiring further interpretation by the operator.

The diagnostic apparatus 23 can also be arranged for transmitting instructions related to controlling of the EGR valve 17 and the BPV 19 to or via the ECU 21. Additionally the diagnostic apparatus 23 can be arranged for transmitting instructions related to the controlling of the diesel fuel doser 25 and exhaust reduction fluid doser 33. In one embodiment the diagnostic apparatus 23 has human interface 49 arranged for allowing for the selection of instructions, by an operator, to be sent to the ECU 21 related to the first state of operation, the second state of operation and the third state of operation of the engine 5. In one embodiment the diagnostic apparatus 23 is further programmed for sending instructions to the ECU 21 relating to creating the initial conditions.

In an alternative embodiment the diagnostic apparatus 23 is further arranged for performing the testing sequence by sending commands related to changing settings for the EGR valve 17 and BPV 19 to the ECU 21.

The method steps of the diagnostic method for diagnosing the first and second $NO_x$-sensor 12, 14 in the diesel engine system 3 as presented in FIG. 2. The diagnostic method comprises steps 1-9 relate to creating the preliminary conditions, steps 10-19 relate to testing of the first and second $NO_x$-sensor 12,14 and steps 20-22 related to the analysis of the data gathered during testing. In Table 2, the steps and designated numbers as seen from FIG. 3 are shown.

TABLE 2

| Reference | Designation |
|---|---|
| 52 | start |
| 53 | step 1 |
| 54 | step 2 |
| 55 | step 3 |
| 56 | step 4 |
| 57 | step 5 |
| 58 | step 6 |
| 59 | step 7 |
| 60 | no |
| 61 | yes |
| 62 | step 8 |
| 63 | no |
| 64 | yes |
| 65 | step 9 |
| 66 | step 10 |
| 67 | step 11 |
| 68 | step 12 |
| 69 | step 13 |
| 70 | step 14 |
| 71 | step 15 |
| 72 | step 16 |
| 73 | step 17 |
| 74 | step 18 |
| 75 | step 19 |
| 76 | step 20 |
| 77 | step 21 |
| 78 | step 22 |
| 79 | end |

In step 1 (reference 53 in FIG. 3) the diesel engine 5 is brought into the first state. Step 1 moves to step 2.

In step 2 (reference 54) the ECU 21 is instructed to close the EGR valve 17 and control the BPV 19 so that the exhaust gas temperature increases sufficiently to heat the DPF 29 to its regeneration temperature. Step 2 moves to step 3.

In step 3 (reference 55) the EGR valve 17 is closed and the BPV 19 is controlled so that the exhaust gas temperature increases sufficiently to heat the DPF 29 to its regeneration temperature. Step 3 moves to step 4.

In step 4 (reference 56) the diesel fuel doser 25 is opened for dosing diesel fuel to the DOC 27. Step 4 moves to step 5.

In step 5 (reference 57) the DPF 29 is regenerated. Step 5 moves to step 6.

In step 6 (reference 58) the pressure over the DPF 29 is measured for determining the progress of the regeneration of the DPF 29. Step 6 moves to step 7.

In step 7 (reference 59) the progress of the regeneration is checked using the pressure sensor 31. After the regeneration is completed step 7 moves to step 8, if the regeneration is not-completed step 7 moves to step 6.

In step 8 (reference 62) the exhaust reduction fluid doser 33 is checked for being open.

When the exhaust reduction fluid doser 33 is found open, step 8 moves to step 9, if the exhaust reduction fluid 33 is found closed step 8 moves to step 10.

In step 9 (reference 65) the exhaust reduction fluid doser 33 is closed to ensure that no exhaust reduction fluid will be present in the exhaust 11. Step 9 moves to step 10.

In step 10 (reference 66) the engine 5 is brought into the second state; Step 10 moves to step 11.

In step 11 (reference 67) the first reading of the values of the first and second $NO_x$-sensor 12, 14 is performed using the ECU 21. Step 11 moves to step 12.

In step 12 (reference 68) the data from the first reading is used to determine the statistical values of the first and second $NO_x$-sensor 12, 14 for the first reading using the diagnostic apparatus 23. Step 12 moves to step 13.

In step 13 (reference 69) the exhaust reduction fluid doser 33 is opened for dosing exhaust reduction fluid into the exhaust 11. Step 13 moves to step 14.

In step 14 (reference 70) the second reading of the value of the second $NO_x$-sensor 14 is performed using the ECU 21. Step 14 moves to step 15.

In step 15 (reference 71) the data from the second reading of the second $NO_x$-sensor is used to determine the statistical values of the second $NO_x$-sensor 14 for the second reading using the diagnostic apparatus 23. Step 15 moves to step 16.

In step 16 (reference 72) the engine 5 is brought into the third state of operation, wherein the BPV 19 and the EGR are restored to normal operations. Step 16 moves to step 17.

In step 17 (reference 73) the second reading of the value of the first $NO_x$-sensor 12 is performed using the ECU 21. Step 17 moves to step 18.

In step 18 (reference 74) the engine 5 is returned to the first state. Step 18 moves to step 19.

In step 19 (reference 75) the data from the second reading of the first $NO_x$-sensor 12 is used to determine the statistical values of the first $NO_x$-sensor 12 for the second reading using the diagnostic apparatus 23. Step 19 moves to step 20.

In step 20 (reference 76) the matrix comprising the predetermined statistical values as seen in Table 1 is created. Step 20 moves to step 21.

In step 21 (reference 77) the analysis of the predetermined values in the matrix is performed using the diagnostic apparatus 23 and the results of the analysis are presented to the operator in the summary of the analysis. Step 21 moves to step 22.

In step 22 (reference 78) the results of the analysis are interpreted by an operator to determine whether there are sufficient indications that the first or second $NO_x$-sensor is malfunctioning. Alternatively in step 22 the diagnostic apparatus 23 determines a first or second $NO_x$-sensor 12, 14 to be malfunctioning when the analysis shows at least one of a first, a second and a third indication of malfunctioning.

In FIG. 4 the diagnostic apparatus 23 is shown to have a communications unit 43. The communication unit 43 can be a communications port arranged for receiving a physical connection such as a communication cable from the ECU 21. In yet another embodiment the communications unit 43 can comprise a cable to connect to a connection port associated with on-board diagnostics. Alternatively the communications unit 43 is arranged for wirelessly receiving from and transmitting information to the ECU 21. The diagnostic apparatus 23 further contains a computer unit 45 arranged for processing received data and performing mathematical operations associated with the analysis. The communications unit 43 is connected to the computer unit 45 for transferring data from the ECU 21. The computer unit 45 is connected to a data storage unit 41 for storing received data and data related to the analysis of the first and second $NO_x$-sensors 12, 14. In one embodiment the data storage unit 41 is a removable memory so as to allow the data to be retrieved and analyzed on a separate computer. The data storage unit 41 can be a non-volatile memory such as a hard drive, a solid state drive, floppy disk, a magnetic tape drive, a non-volatile RAM, a ROM cartridge, a flash drive, micro SD card or a data card. The data storage unit 41 is used to store predetermined statistical values associated with the related diesel engine system 3. The data storage unit 41 is preprogrammed to contain a computer program which can be accessed by the computer unit 45 of the diagnostic device for performing the analysis. The data storage unit 41 further contains the predetermined statistical values associate with the diesel engine system 3. Further, the data storage unit 41 is reprogrammable to be updated to contain the predetermined statistical values associated with a diesel engine systems 3 for when the diagnostic apparatus is used for more than one single type diesel engine system 3. Alternatively the data storage unit 41 comprises the predetermined statistical values for a plurality of diesel engine systems 3. The computer unit 45 is programmed to determine by means of operator input or by information obtained from the ECU 21 which predetermined statistical values are relevant to the diesel engine system 3 so the predetermined statistical values are that of the associated diesel engine system 3. The computer unit 45 is further connected to the display 47 and the human interface 49. The computer unit 45 is a preprogrammed computer processor, wherein the computer unit 45 is arranged for being connected to the interface 49 and for receiving instructions from the operator. The interface 49 can alternatively also be part of the display 47, then being in a form of a touch screen. The diagnostic apparatus 23 is specifically arranged for use in a workshop, and is alternatively arranged to contain its own power supply 51 such as a battery for enhanced mobility. In yet another embodiment the diagnostic apparatus 23 can be an onboard system and then would be permanently present in the same vehicle as the diesel engine system 3.

Accordingly a method and apparatus have been disclosed for field testing and diagnosing at least one $NO_x$-sensor in a diesel engine exhaust system. The field testing apparatus being connectable to a truck having a lean burn diesel type engine, via an on-board diagnostic connector. The field testing apparatus is arranged to initiate a test cycle, and to diagnose at least one $NO_x$-sensor in an exhaust system of the truck. The test cycle is performed on a running engine as a test sequence in a stationary truck, in at least two different states of operation, while $NO_x$ related values issued by the at least one $NO_x$-sensor are measured over a predefined period of time. At least one state of operation is obtained by simultaneously opening the exhaust gas recirculation valve and controlling the back pressure valve for increasing backpressure. A dedicated algorithm is used to compare the measured values to a predefined model, and to provide a numerical summary and statistical evaluation of the sensor functioning. The numerical summary being indicative of a likelihood of the at least one $NO_x$-sensor behaving correctly, and thereby enables a well founded decision as to whether or not the at least one $NO_x$-sensor requires replacement.

The present invention has been described in terms of some specific embodiments thereof. It will be appreciated that the embodiments shown in the drawings and described herein are intended for illustrated purposes only and are not by any manner or means intended to be restrictive on the invention. The context of the invention discussed here is merely restricted by the scope of the appended claims.

What is claimed is:

1. A method for diagnosing at least one $NO_x$-sensor in a diesel engine system that includes a diesel engine, an exhaust gas treatment system, and an electronic engine control unit configured to receive sensor readings from the at least one $NO_x$-sensor, and to control running of the diesel engine in a plurality of different states of operation, at least partly in response to the sensor readings, wherein the exhaust gas treatment system comprises an exhaust gas recirculation system connecting an exhaust to an inlet via an exhaust gas recirculation valve, the exhaust comprises a back pressure valve, the method comprising providing a diagnostic apparatus, communicatively connecting the diagnostic apparatus to the electronic engine control unit, performing a testing sequence by allowing the diagnostic apparatus to send commands to the electronic engine control unit and performing a diagnostic analysis on the at least one $NO_x$-sensor, the testing sequence comprising:

running the engine in one state of operation, with one $NO_x$ production level;

obtaining a first values reading of the at least one $NO_x$-sensor over a predefined time interval using the electronic control unit;

running the diesel engine in another state of operation, different from the one state of operation, with another $NO_x$ production level, wherein the other $NO_x$ production level is lower than the one $NO_x$ production level, wherein the other state of operation is obtained by opening the exhaust gas recirculation valve and controlling the back pressure valve for controlling the backpressure; and obtaining a second values reading of the at least one $NO_x$-sensor over another predefined time interval using the electronic control unit and the diagnostic analysis comprising:

forming statistical values using the first and second values readings of the at least one $NO_x$-sensor;

comparing the statistical values to stored predefined statistical values from a predefined model; and determining the functioning of the at least one $NO_x$-sensor.

2. The method of claim 1, wherein the at least one $NO_x$-sensor is one of a first and a second $NO_x$-sensor.

3. The method of claim 2, wherein the first $NO_x$-sensor is positioned upstream of an exhaust gas treatment system.

4. The method of claim 2, wherein the second $NO_x$-sensor is positioned downstream of the exhaust gas treatment system.

5. The method of claim 1, wherein the exhaust gas treatment system further comprises:

a diesel fuel doser; a diesel oxidation catalyst; a diesel particulate filter; an exhaust reduction fluid doser; a selective catalyst reduction system; an ammonia oxidation catalyst; and wherein the second $NO_x$-sensor is located downstream of the ammonia oxidation catalyst in the exhaust; and the method further comprises testing steps of:

obtaining a first reading of the second $NO_x$-sensor values over a predefined time interval using the electronic control unit, wherein the engine is in the one state of operation;

activating the exhaust reduction fluid doser, for dosing of exhaust reduction fluid into the exhaust; and obtaining a second reading of the second $NO_x$-sensor values over yet another predefined time interval using the electronic control unit.

6. The method of claim 5, wherein the exhaust gas treatment system further comprises:

a differential pressure sensor configured for measuring the pressure difference over the diesel particulate filter; and the method comprises:

a step of creating preliminary conditions before the testing steps, wherein the step of creating the preliminary conditions comprises: running the diesel engine in a preliminary state of operation, wherein the diesel runs idle at a first temperature; instructing the electronic control unit to close the exhaust gas recirculation valve; causing the exhaust gas recirculation valve to close; controlling the back pressure valve for increasing the temperature of the exhaust gas from the first temperature to a temperature sufficiently high for soot to be burned off from the diesel particulate filter; checking whether the diesel fuel doser is open; opening the diesel fuel doser when found closed, for supplying diesel to the diesel oxidation catalyst using the electronic control unit; regenerating the diesel particulate filter; measuring the pressure difference over the diesel particulate filter using the differential pressure sensor, and using the electronic control unit for checking whether the exhaust reduction fluid doser is open; and for closing the exhaust reduction fluid doser when found open.

7. The method of claim 1, further comprising data analysis of the at least one $NO_x$-sensor, wherein the data analysis comprises the steps of:

using the first and second values readings of the at least one $NO_x$-sensor to determine statistical values of the at least one $NO_x$-sensor;

placing the statistical values in a matrix;

comparing the statistical values to stored predefined statistical values from a predefined model; and determining the functioning of the at least one $NO_x$-sensor.

8. The method of claim 7, wherein the at least one $NO_x$-sensor is one of a first and a second $NO_x$-sensor, and the statistical values comprise a value representative of a statistical minimum, and a value representative of a statistical maximum of each of the first and second $NO_x$-sensors at a first and second reading thereof.

9. The method of claim 8, further comprising comparing the statistical values to a predefined model comprising:

using a statistical algorithm to establish a measure of linear correlation between the statistical values and the stored predefined statistical values, wherein the manner of linear correlation is expressed in a correlation coefficient;

performing a linearity test; and determining linear deviation.

10. The method of claim 9, wherein the statistical algorithm used to establish a measure of linear correlation between the statistical values and the stored predefined statistical values is a Pearson algorithm, and wherein the correlation coefficient is the product-moment correlation coefficient.

11. The method of claim 9, wherein determining the linear deviation further comprises expressing the linear deviation as the deviation of statistical values from the predetermined statistical values, wherein the linear deviation is expressed in percentile deviation from the predetermined statistical values.

12. The method of claim 7, further comprising:

expressing a series of points in two-dimensional coordinates, wherein each point is formed by expressing a statistical value as a first dimensional part of the coordinates of the point and the predetermined statistical value as a second dimensional part of the coordinates of the point; and fitting a first order equation using a method of least squares to the series of points, wherein the coefficient of determination is used to determine the linearity of the series of points.

13. An apparatus for diagnosing at least one $NO_x$-sensor in a diesel engine system that includes a diesel engine, an exhaust gas treatment system, and an electronic engine control unit configured to receive sensor readings from the at least one $NO_x$-sensor, and to control running of the diesel engine in a plurality of different states of operation, at least partly in response to the $NO_x$-sensor readings, wherein the diagnostic apparatus is communicatively connectable to the electronic engine control unit, wherein the diagnostic apparatus is configured for performing a testing sequence by sending commands to the electronic engine control unit and for performing a diagnostic analysis on the at least one $NO_x$-sensor, wherein the testing sequence comprises:

running the engine in at least two different states of operation, each having a different $NO_x$ production level over a predefined time interval;

wherein the diagnostic analysis comprises:

obtaining first and second readings of the at least one $NO_x$-sensor;

forming statistical values using the first and second readings of the at least one $NO_x$-sensor;

comparing the statistical values to stored predefined statistical values from a predefined model; and determining the functioning of the at least one $NO_x$-sensor, wherein the diagnostic analysis further comprises placing the statistical values obtained from the first and second readings of the at least one $NO_x$-sensor in a matrix, prior to said comparing of the statistical values to stored predefined statistical values.

14. The apparatus of claim 13, wherein the at least one $NO_x$-sensor is one of a first and a second $NO_x$-sensor.

15. The apparatus of claim 14, wherein the first $NO_x$-sensor is positioned upstream of an exhaust gas treatment system.

16. The apparatus of claim 14, wherein the second $NO_x$-sensor is positioned downstream of the exhaust gas treatment system.

17. The apparatus of claim 13, adapted for connection to a diesel engine system that includes a back pressure valve, and further being configured for sending instructions to the electronic engine control unit for controlling the back pressure valve.

18. The apparatus of claim 17, adapted for connection to a diesel engine system that includes an exhaust gas recirculation system connecting an exhaust to an inlet via an exhaust gas recirculation valve, and further being configured for sending instructions to the electronic engine control unit for controlling the exhaust gas recirculation valve.

19. The apparatus of claim 13, adapted for connection to a diesel engine system that includes a diesel fuel doser and an exhaust reduction fuel doser, and further being configured for sending instructions to the electronic engine control unit for controlling the diesel fuel doser and the exhaust reduction fluid doser.

20. The apparatus of claim 13, further configured for relaying to an operator information pertaining the functioning of the at least one $NO_x$-sensor.

21. A diagnostic system comprising a diesel engine system, including a diesel engine, having an inlet, an exhaust and an exhaust gas treatment system, and an exhaust gas recirculation system connecting the exhaust to the inlet, wherein the exhaust comprises a back pressure valve, and wherein the exhaust gas recirculation system comprises an exhaust gas recirculation valve; at least one $NO_x$-sensor located downstream of the back pressure valve in the exhaust; and an electronic engine control unit configured for reading the at least one $NO_x$-sensor, for controlling the exhaust gas recirculation valve and for controlling the back pressure valve; wherein the diagnostic system further comprises a diagnostic apparatus configured for being communicatively connectable to the electronic engine control unit of the diesel engine system, and wherein the diagnostic apparatus comprises a computer unit configured for obtaining, in one state of operation with the engine running with one $NO_x$ production level, a first values reading of the at least one $NO_x$-sensor over a predefined time interval using the electronic control unit;

obtaining, in another state of operation different from the one state of operation and with the engine running with another $NO_x$ production level lower than the one $NO_x$ production level, a second values reading of the at least one $NO_x$-sensor over another predefined time interval using the electronic control unit, wherein the other state of operation is obtained by opening the exhaust gas recirculation valve and controlling the back pressure valve for controlling the backpressure;

forming statistical values using the first and second values readings of the at least one $NO_x$-sensor;

comparing the statistical values to stored predefined statistical values from a predefined model; and determining the functioning of the at least one $NO_x$-sensor.

* * * * *